(12) United States Patent
Magnani et al.

(10) Patent No.: US 7,645,788 B2
(45) Date of Patent: Jan. 12, 2010

(54) TETRAMEROUS DERIVATIVE OF INDOLE-3-CARBINOL WITH ANTI-CARCINOGENIC ACTIVITY AND METHOD OF SYNTHESIS OF SAID DERIVATIVE

(75) Inventors: Mauro Magnani, Urbino (IT); Chiara Fiorucci, Urbino (IT); Paolino Filippone, Urbino (IT); Giorgio Brandi, Urbino (IT); Mirko Paiardini, Urbino (IT)

(73) Assignee: Universita' Degli Studi Di Urbino, Urbino (IT)

( * ) Notice: Subject to any disclaimer, the term of this patent is extended or adjusted under 35 U.S.C. 154(b) by 890 days.

(21) Appl. No.: 10/479,551

(22) PCT Filed: Jun. 5, 2002

(86) PCT No.: PCT/IT02/00368

§ 371 (c)(1), (2), (4) Date: Jun. 9, 2004

(87) PCT Pub. No.: WO02/098881

PCT Pub. Date: Dec. 12, 2002

(65) Prior Publication Data

US 2004/0214876 A1    Oct. 28, 2004

(30) Foreign Application Priority Data

Jun. 6, 2001    (IT) .......................... MI2001A1196

(51) Int. Cl.
*A61K 31/407* (2006.01)
(52) U.S. Cl. .................. 514/410; 548/455; 548/469
(58) Field of Classification Search .......... 514/410; 548/455, 469
See application file for complete search history.

(56) References Cited

OTHER PUBLICATIONS

Gross, Karl R. et al: "Oligomerization of indole-3-carbinol in aqueous acid" Chemical Research in Toxicology; ISSN 0893-228X vol. 5, No. 2, pp. 188-193, XP002218242 Ctet' scheme II.

Riby J.E. et al.: "The Major Cyclic Trimeric Product of Indole-3-Carbinol is a Strong Agonist of the Estrogen Receptor Signaling Pathway" Biochemistry, American Chemical Society. Easton, PA, US, vol. 39, No. 5, 2000, pp. 910-918, XP000983790 ISSN: 0006-2960 abstract.

*Primary Examiner*—Yong Chu
(74) *Attorney, Agent, or Firm*—Ladas and Parry LLP

(57) ABSTRACT

Use of the tetramerous derivative of indole-3-carbinol having formula I

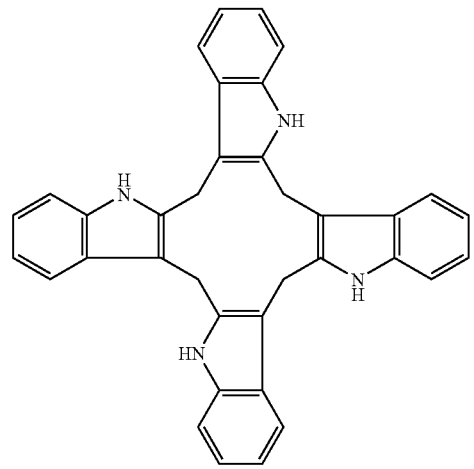

for preparing a medicinal having anti-carcinogenic activity, and method of synthesis of the tetramerous derivative having formula I, in which indole-3-carbinol is reacted with an oxidizing agent so as to cause a polymeric oxidation of indole-3-carbinol.

3 Claims, 4 Drawing Sheets

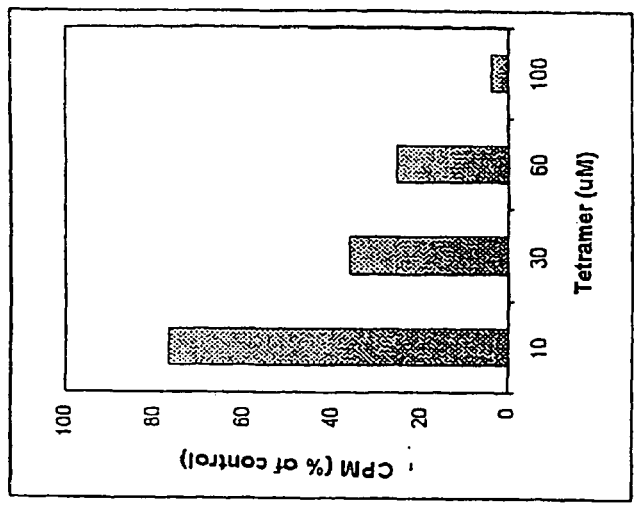
Figure 2: Anti-proliferative activity of tetramer in breast cancer line MDA-MB-234, evaluated by Incorporation of tritium-added thymidine into cell DNA
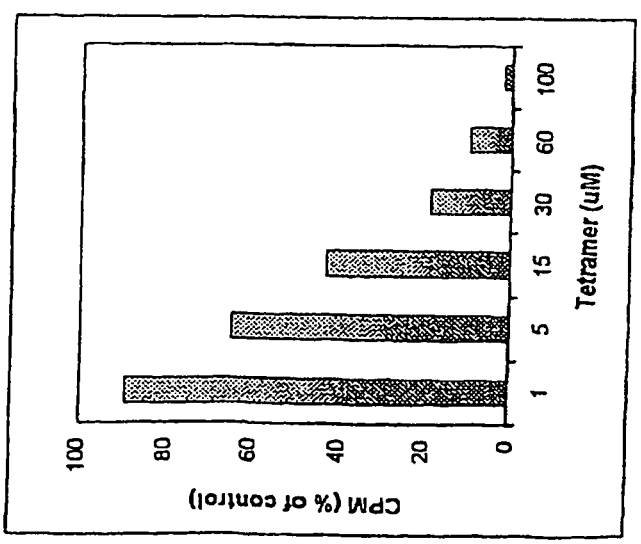
Figure 1: Anti-proliferative activity of tetramer in breast cancer line MCF-7, evaluated by Incorporation of tritium-added thymidine into cell DNA Repressed transcription Transcription of genes
from S stage

TETRAMEROUS DERIVATIVE OF INDOLE-3-CARBINOL WITH ANTI-CARCINOGENIC ACTIVITY AND METHOD OF SYNTHESIS OF SAID DERIVATIVE

The application Ser. No. 10/479,551 filed on Jun. 9, 2004 which is a 371 of PCT/IT02/00368 filed Jun. 5, 2002 which claims the benefit thereof and incorporates the same by reference.

TECHNICAL FIELD

The present invention relates to the use of a tetramerous derivative of indole-3-carbinol for preparing a medicinal having anti-carcinogenic activity.

The present invention further relates to a method of synthesis of the tetramerous derivative of indole-3-carbinol.

BACKGROUND ART

It has been known for a long time that plants belonging to the family of cruciferae contain substances acting on the growth of tumoral cells, and whose administration thus reduces the effects of cancer onto the human body.

The anti-carcinogenic properties of these plants have been found both through epidemiological evidence and by means of tests carried out on animals. Such anti-carcinogenic properties can be attributed to the presence of nutritive and non-nutritive constituents such as indole glucosinates, which are known as inhibitors of the carcinogenic process.

Indole-3-carbinol is a product deriving from the spontaneous hydrolysis of the indole glucosinate gluco-brassicin contained in plants belonging to the family of Cruciferae. Indole-3-carbinol is supposed to be an inhibitor both of breast cancer induced in rats by dimethylbenzanthracene and of stomach cancer induced by benzo(a)pyrene. Once formed, Indole-3-carbinol under-goes further photoinduced transformations with formation of polymeric degradation products.

Some of such polymeric products and their preparation are reported in the article "Oligomerization of Indole-3-carbinol in aqueous acid" by GROSE, Karl et al. in CHEMICAL RESEARCH IN TOXICOLOGY; ISSN 0893-228X, vol. 5, no. 2, 1992, pages 188-193; biological activity of the trimeric product is reported in the article "The major cyclic trimeric product of Indole-3-cabinol is a strong agonist of the estrogen receptor signalling pathway" by RIBY J et al. in BIOCHEMISTRY, Americam Chemical Society, Easton, Pa., US, vol. 39, no. 5, 2000, pages 910-918.

The authors of the present invention have unexpectedly and surprisingly found that a tetramerous derivative of indole-3-carbinol has a high anti-carcinogenic activity. In particular, it has been found that the anti-carcinogenic activity of the tetramerous derivative develops independently from the presence of estrogen receptors in tumoral cells.

DISCLOSURE OF INVENTION

Therefore, an object of the present invention is the use of the tetramerous derivative having formula I

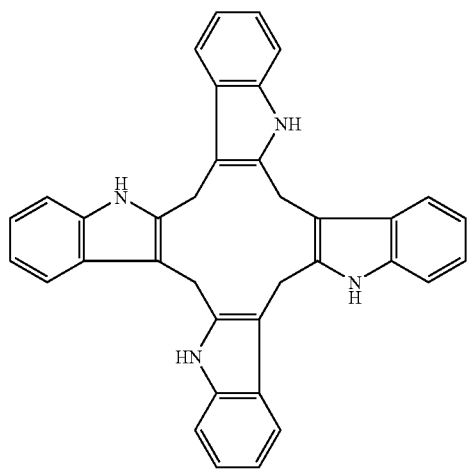

for preparing a medicinal having anti-carcinogenic activity, according to Claims 1 and 4.

A further object of the present invention is a method of synthesis of the tetramerous derivative of indole-3-carbinol having formula I, said method being characterized in that indole-3-carbinol is reacted with an oxidizing agent so as to cause a selective polymeric oxidation of indole-3-carbinol.

Such oxidation reaction is carried out at room temperature.

The oxidation reaction takes place by using an oxidizing agent chosen in the group consisting of: potassium permanganate, potassium dichromate, acetic acid, phosphoric acid, phosphorus oxychloride, hydrogen peroxide, cupric chloride and iodine.

The oxidation reaction occurs in presence of a solvent chosen in the group consisting of ethyl ether, ethyl acetate, acetonitrile, methanol, ethanol and water. It is preferable to use an organic solvent, and the solvent used is preferably either methanol or ethanol. In fact, whereas water does not solubilize the monomer and the reaction takes place in the interface water-organic ambient, in organic solvents the monomer solubilizes and the oxidation reaction leads to yields of tetramerous derivative which are far higher that those obtained with the reaction in water.

The method of synthesis further comprises a purification stage, preferably such purification is obtained by means of a chromatographic column and/or by means of crystallization from alcohol.

A final object of the present invention is the tetramerous derivative having formula I obtained in purified form by means of the synthesis described above.

BRIEF DESCRIPTION OF THE DRAWINGS

The following examples disclose in further detail and without limitations the method of synthesis for preparing the tetramerous derivative having formula I together with the assays carried out for determining the anti-carcinogenic activity of said tetramerous derivative. The examples refer to the following figures:

FIG. 1 shows through a chart the anti-carcinogenic activity of the tetramerous derivative of indole-3-carbinol on lines of breast cancer cells expressing estrogen receptors;

FIG. 2 shows through a chart the anti-carcinogenic activity of the tetramerous derivative of indole-3-carbinol on lines of breast cancer cells which are negative for estrogen receptors;

PREFERRED EMBODIMENTS OF THE INVENTION

EXAMPLE 1

Figure 4:
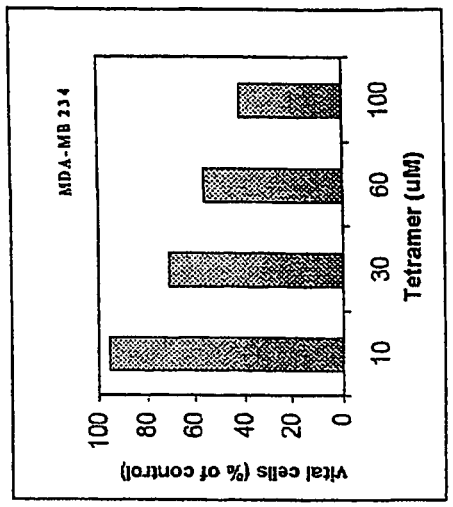
FIG. 4 shows through a chart the percentage of vital breast cancer cells which are negative for estrogen receptors in relation to the amount of the tetramerous derivative of indole-3-carbinol administered.

Synthesis of the Tetramerous Derivative of Indole-3-Carbinol

Chemical Synthesis 1a 1 g of indole-3-carbinol is dissolved in 20 ml of methanol, then added with iodine in catalytic amount (5:1) and placed under stirring at room temperature. After 5 minutes a precipitate forms, which is filtered and suitably purified.

In particular, the raw product obtained from the reaction is evaporated under reduced pressure by means of a rotavapor and extracted three times with ethyl acetate and water in a separatory funnel. The organic extract is dried on anhydrous sodium sulphate, filtered and evaporated, then purified in a column of silica gel in cyclohexane, eluted with cyclohexane/ethyl acetate mixtures up to a ratio of the two solvents of 5:5.

The tetramerous derivative obtained can be recrystallized from ethyl ether/methanol.

The structure of the product obtained with almost quantitative yields has been confirmed by spectroscopic methods. IR, NMR and MS spectra are registered respectively on Nicolet Impact 400, on a Varian at 400 MHz and on a Shimadzu QP-5000 at a ionization potential of 70 eV.

The following spectroscopic data refer to the pure product:
IR: 3400, 2958, 2933, 2905, 2852, 1460, 1379, 745 cm$^{-1}$
Ms: 516 [M$^+$], 504, 387, 375 (100), 258 (100), 245, 130
$^1$H-NMR: DMSO-d$_6$ ($\delta$): 4.18 (m), 5.37 (m), 6.70-7.60 (m), 10.70 (m) $^{13}$CH-NM: CDCL$_3$ ($\delta$): 21.2, 107.4, 111.0, 119.5, 120.2, 122.3, 128.8, 135.3, 136.8

Chemical Synthesis 1b 1 g of indole-3-carbinol is dissolved in 20 ml of ethanol, then added with anhydrous CuCl$_2$ in catalytic amount (r=5:1) and placed under magnetic stirring at room temperature. After 15 minutes indole-3-carbinol has completely disappeared, as can be observed by TLC on silica gel eluted in 5:5 of cyclohexane-ethyl acetate, with the formation of a predominant high spot corresponding to the tetramerous derivative and of other spots at an intermediate height between the starting reagent and the tetramerous derivative, corresponding to trimerous derivatives.

Product filtration and purification are carried out following the method described in Chemical synthesis 1a.

The yield is of about 70% of tetramerous derivative with 20% of trimer and 10% of impurities.

Other Chemical Syntheses

Oxidation reactions of indole-3-carbinol are carried out also with dihydrated CuCl$_2$, with POCl$_3$ and with I$_2$ at 0° C. and under reflux in ethanol, all reactions resulting in good yields of tetramerous derivative and developing similarly to the description above.

At the state of the art the best conditions have proved to be those involving the treatment of indole-3-carbinol with I$_2$ or with CuCl$_2$ in an alcoholic solvent.

EXAMPLE 2

Evaluation Assay of the Anti-Proliferative Effect of the Tetramerous Derivative in Lines of Human Mammary Carcinoma The activity of the tetramerous derivative has been evaluated both in breast cancer cells grown in laboratory expressing estrogen receptors (line MCF-7) and in cells which are negative for said receptors (line MDA-MB-234).

MCF-7 and MDA-MB-234 cells have been grown in laboratory in a DMEM medium added with 10% of bovine fetal serum, 1% of a penicillin-streptomycin solution, 1% of a solution of non-essential amino acids, 2 mM glutamine and for MCF-7 also with 10 ug/ml of insulin. For the tests the cells are taken and used in their logarithmic growth phase, suspending them again the same fresh medium and exposing them to the tetramerous derivative up to 72 hours at 37° C. in an atmosphere with 5% of CO$_2$. Before the treatment the cells are grown for some hours so as to adhere well to the plastic and start proliferating. In the tests concerning the evaluation of the anti-proliferative activity the synthesis of DNA is evaluated by adding to the cultures 3 µCi/ml of [3H]-thymidine 6 hours before the end of the treatment.

The cells are exposed during the culture to increasing concentrations of tetramerous derivative, then evaluating the degree of inhibition of their proliferation by incorporating into the DNA tritium-added thymidine (Cover C. M. et al., 1998, *Journal of Biological Chemistry* no. 273, page 3838-3847). As can be seen from FIG. 1 and FIG. 2, the tetramerous derivative inhibits in a dose-dependent way the cell proliferation both of line MCF-7 and of line MDA-MB-234, thus showing a similar activity in both lines.

In a second set of tests the activity of the tetramerous derivative on the two cell lines has been evaluated as cytotoxicity using a method (Magnani M. et al., 1995, *Biochemical Journal* no. 312, page 115-123) which allows to recognize vital from dead cells.

MCF-7 and MDA-MB-234 cells have been grown as previously described. Then, after 24 and after 72 hours of exposition to the tetramerous derivative they are taken and counted in duplicate in a hemocytometer using trypan blue dye to exclude dead cells.

Figure 3:
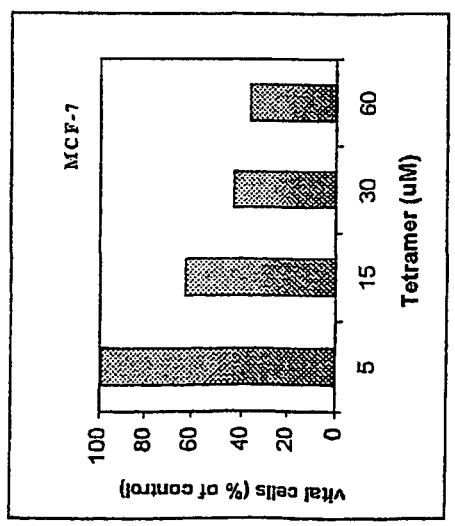
FIG. 3 shows through a chart the percentage of vital breast cancer cells expressing estrogen receptors in relation to the amount of the tetramerous derivative of indole-3-carbinol administered.
Figure 5:
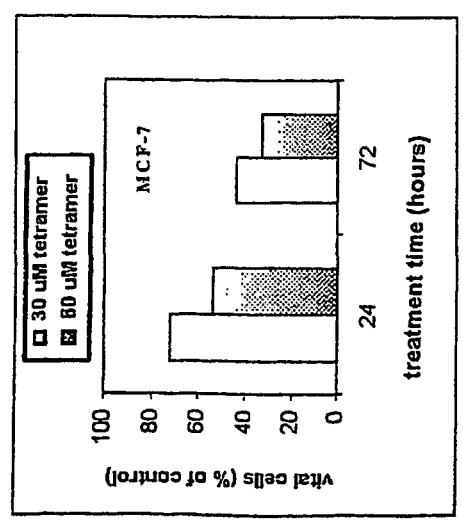
FIG. 5 shows through a chart the percentage of vital breast cancer cells expressing estrogen receptors in relation to the time of administration of the tetramerous derivative of indole-3-carbinol.

As can be seen in FIGS. 3, 4 and 5, also in this case a dose-dependent (FIG. 3 e 4) as well as time-dependent (FIG. 5) toxicity can be observed.

The results obtained show that the tetramerous derivative is highly active as inhibitor of the growth of lines of human mammary carcinoma and that such activity is independent from the presence of estrogen receptors.

EXAMPLE 3

Determination of Molecular Mechanisms Causing the Anti-Proliferative Effect of the Tetramerous Derivative The purpose of the research has been to identify the molecular targets on which the tetramerous derivative acts reducing the proliferative activity in breast cancer cells independently from the presence of estrogen receptors.

SDS-PAGE (Laemmli U.K. 1970, *Nature* 227, 680-685) and Western Blot (Towbin H., Staehelin T., Gordon J. 1979, *Proc. Natl:Acad. Sci. USA* 76, 4350-4354) techniques have been used to analyze the expression of proteins known as fundamental targets (markers) in the control of the cellular cycle, whose modifications often lead to an uncontrolled cell proliferation: cyclin-dependent kinase cdk6 (Cover C. M., et al, 1998, *J. Biol. Chem.* 273, 3838-3847), inhibitor p27 (Wang X., et al., 1997, *Oncogene* 15, 2991-2997; Vidal A., Koff A. 2000, *Gene* 247, 1-15) and retinoblastoma Rb (Dyson N. 1998, *Genes & Development* 12, 2245-2262; Guardavaccaro D., et al., 2000, *Mol. Cell. Biol.* 20 (5), 1797-1815).

After growing the cells as previously described, the cell cultures undergo the action of increasing doses of tetramerous derivative. Then culture samples are taken and the cells are lysated with B buffer (Hepes 20 mM pH 7.5, NaCl 420 mM, MgCl2 1.5 mM, EDTA 0.2 mM, glycerol 25%) in presence of antiproteolytic agents Nonidet P40 0.5% (v/v), kept under ice for 20 minutes and centrifuged at 12,000 rpm for 10 minutes at 4° C.

The cell lysate (supernatant liquor) is then diluted 1:1 with Sample Buffer 2× and charged into SDS-PAGE at 12% of acrylamide following Laemmli's method (Laemmli U.K. 1970, *Nature* 227, 680-685).

The proteins thus separated are then transferred onto a nitrocellulose membrane according to Towbin's method (Towbin H., Staehelin T., Gordon J. 1979, *Proc. Natl:Acad. Sci. USA* 76, 4350-4354); said membrane is blocked with a solution of TBS+5% milk, incubated for the whole night at 4° C. with anti-cdk6 (1:200), anti-p27 (1:500), anti-pRb (1:200) antibodies purchased from Santa Cruz Biotechnology.

The membrane is washed 3 times with TBS+0.08% Tween 20 for 8 minutes at room temperature and incubated for 1 hours with anti-mouse goat antibody or anti-rabbit goat antibody (1:4000) conjugated with peroxidase. Chemiluminescence is used as detection system.

Figure 6:
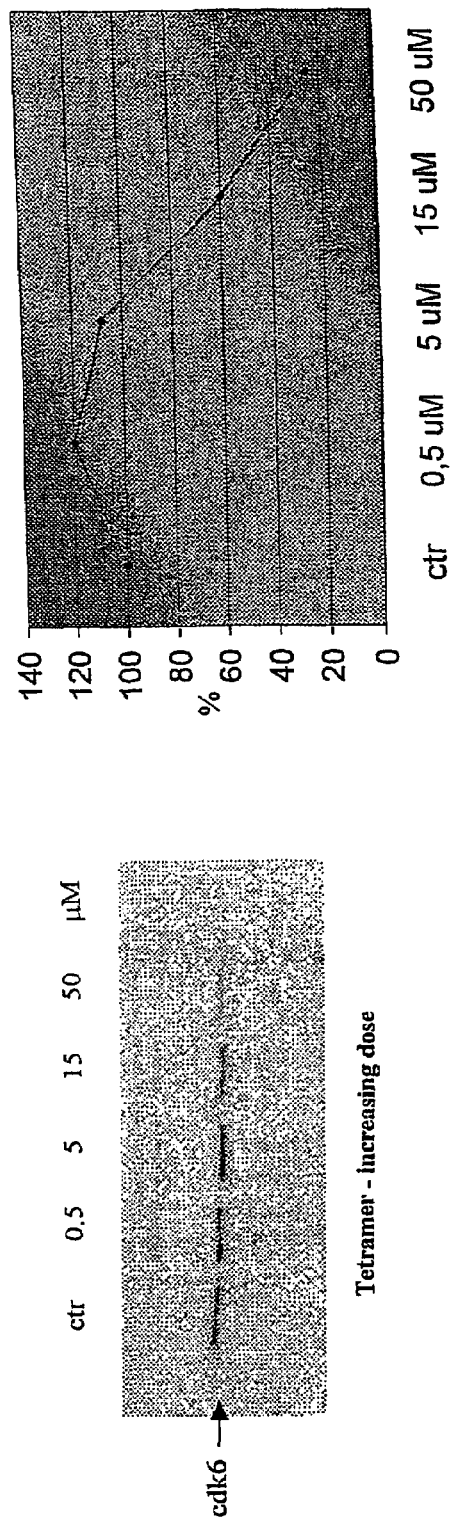
FIG. 6 shows through a chart the behavior of enzyme cdk6 in relation to the presence of the tetramerous derivative of indole-3-carbinol.

First of all the level of expression of cdk6 in MCF-7 treated with increasing doses of tetramerous derivative is quantified: as shown in FIG. 6 a great reduction of said enzyme can already be observed with a dose of tetramerous derivative of 15 µM, and a sudden decrease can be found at 50 µM.

Figure 7:
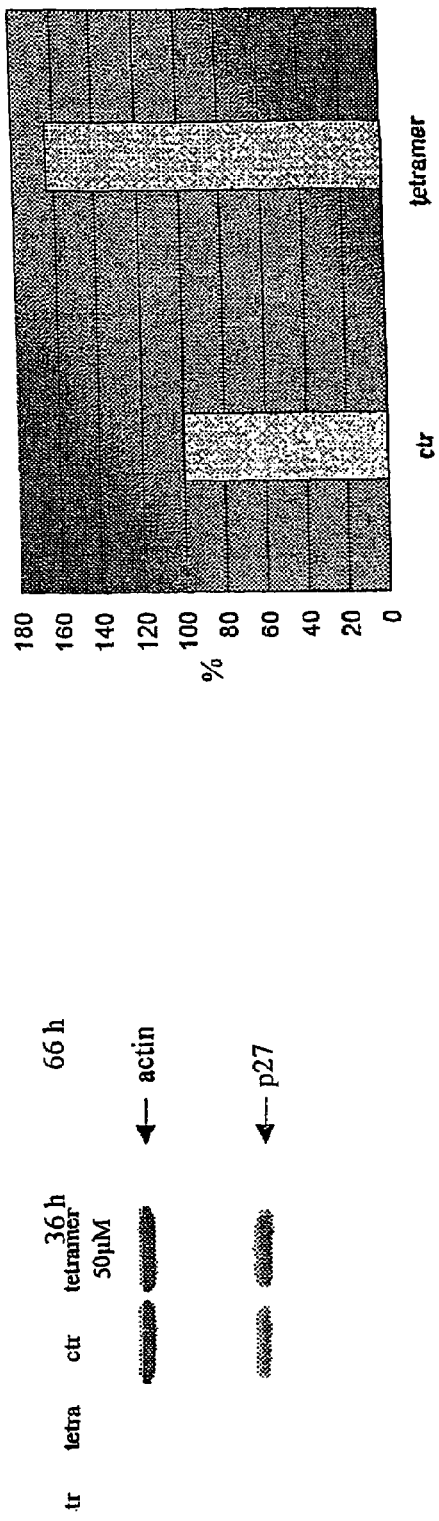
FIG. 7 shows through a chart the behavior of protein p27 in relation to the presence of the tetramerous derivative of indole-3-carbinol.
Figure 8:
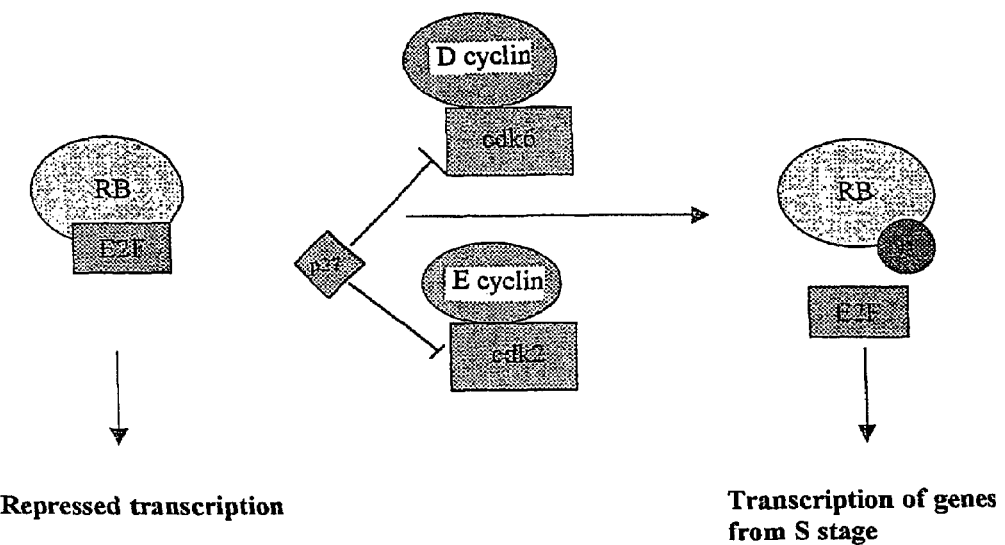
FIG. 8 schematically shows the regulation carried out by enzyme cdk6 and by protein p27 on the phosphorylation of Rb factor.

Western blot technique is again used to detect the level of protein p27 inhibiting the complexes D cyclin-cdk6 and E cyclin-cdk2: p27 increases when the same concentrations of tetramerous derivative are used (FIG. 7).

cdk6 and the inhibiting protein p27, as can be see from the chart in FIG. 8, regulate the phosphorylation of Rb factor enabling, through E2F factor, G1/S transition.

The following step is then to verify whether the anti-proliferating activity of the tetramerous derivative is due to a modification in the level of phosphorylation of Rb factor caused by the reduction of cdk6 and by the increase of p27.

This is why the tests carried out as previously indicated are used to verify, always by means of Western Blot, also the level of pRb through the use of a suitable antibody. The results obtained are shown in FIG. 9.

Figure 9:
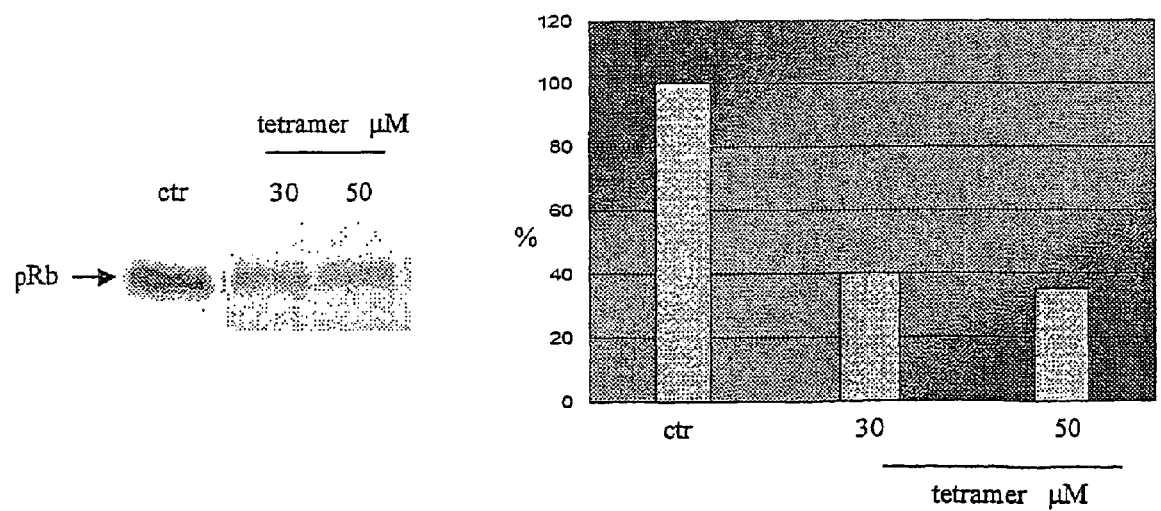
FIG. 9 shows through a chart the behavior of the phosphorylation of Rb factor in relation to the presence of the tetramerous derivative of indole-3-carbinol.

As can be seen in FIG. 9, the use of the tetramerous derivative can highly reduce (inhibition of 60%) such phosphorylation already at a concentration of 30 µM.

Said markers are then evaluated as previously described on estrogen-negative cell line MDA-MB-234. The tests carried out show that also in these cells there is a reduction of enzyme cdk6 and an increase of inhibitor p27. This result indicates that the anti-proliferating action of said molecule is independent from the presence of the estrogen receptor and makes it suitable for the treatment of both populations (estrogen-positive and estrogen-negative) of breast cancer cells.

The invention claimed is:

1. A method for treating breast cancer comprising administering an effective amount of tetramerous derivative of indole-3-carbinol of formula I

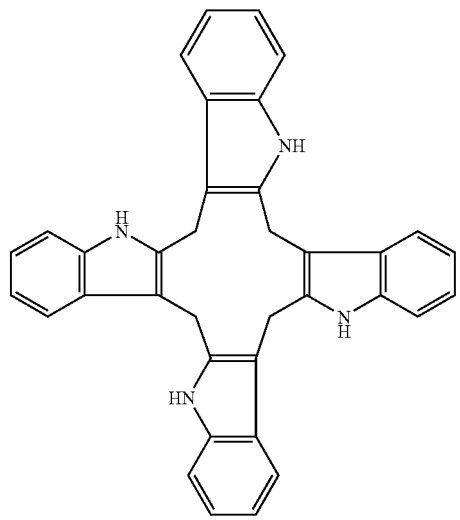

to a patient in need thereof.

2. The method according to claim 1, wherein the breast cancer comprises breast cancer cells which are both estrogen-dependent and estrogen-negative in their growth.

3. A method for inhibiting growth of breast cancer cells which are both estrogen-dependent and estrogen-negative in their growth which comprises administering an effective amount of a tetramerous derivative of indole-3-carbinol of formula I

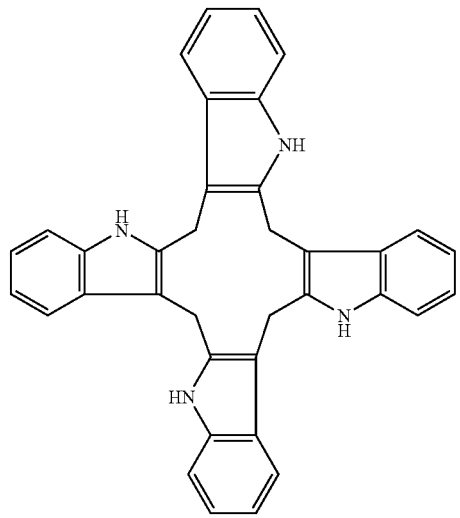

to a patient in need thereof.

* * * * *